United States Patent [19]

Pope et al.

[11] Patent Number: 5,272,260
[45] Date of Patent: Dec. 21, 1993

[54] REAGENTS AND METHODS FOR THE DETERMINATION OF GLYCOHYDROLYTIC ENZYMES

[75] Inventors: Mark R. Pope, Wildwood; Christopher Bieniarz, Highland Park, both of Ill.

[73] Assignee: Abbott Laboratories, Abbott Park, Ill.

[21] Appl. No.: 827,669

[22] Filed: Jan. 29, 1992

[51] Int. Cl.$^5$ .................. C07H 15/24; C12Q 1/00
[52] U.S. Cl. ...................... 536/18.1; 435/4; 435/7.4; 435/7.7; 436/800; 436/808
[58] Field of Search .............. 536/18.1; 435/4, 7.4, 435/7.7; 436/800, 808

[56] References Cited

U.S. PATENT DOCUMENTS

| | | | |
|---|---|---|---|
| 4,830,961 | 5/1989 | Petty | 436/800 |
| 4,912,208 | 3/1990 | Fiechtner et al. | 536/53 |
| 5,102,808 | 4/1992 | Petty | 435/7.21 |

*Primary Examiner*—Ronald W. Griffin
*Attorney, Agent, or Firm*—Daniel W. Collins; James L. Wilcox

[57] ABSTRACT

Novel pyrene-trisulfonate derivatives and the use thereof in a method for the determination of glycohydrolytic enzyme activity are provided. The method comprises the steps of (a) forming a test solution comprising a test sample containing the glycohydrolytic enzyme and a pyrene-trisulfonate derivative of the present invention, wherein the derivative is hydrolyzed by the glycohydrolytic enzyme to result in the formation of free 8-hydroxy-1,3,6-pyrene trisulfonate as a function of, and which can be correlated to, the amount of the glycohydrolytic enzyme present in the test sample, and (b) measuring and correlating either the intensity of fluorescence, or the optical density, of the test solution to the presence or amount of the glycohydrolytic enzyme in the test sample. A preferred pyrene-trisulfonate derivative is pyrene-(1,3,6-trisulfonic acid)-8-$\beta$-D-glucuronide for the determination of $\beta$-D-glucuronidase for the diagnosis of periodontal disease.

16 Claims, 3 Drawing Sheets

REAGENTS AND METHODS FOR THE DETERMINATION OF GLYCOHYDROLYTIC ENZYMES

FIELD OF THE INVENTION

The present invention relates to the determination of glycohydrolytic enzymes. In particular, the present invention relates to pyrene-trisulfonic acid derivatives of carbohydrates and the use thereof in assays for the determination of glycohydrolytic enzymes such as $\beta$-glucuronidase.

BACKGROUND OF THE INVENTION

Glycohydrolytic enzymes are a class of enzymes which have been employed in various diagnostic applications, such as for measuring PMN phagocytic activity and periodontal disease activity, for classifying bacteria, and as a component of conjugates in enzyme immunoassay procedures. Conventionally, the determination of glycohydrolytic enzymes, particularly $\beta$-glucuronidase, involves the use of a hydrophobic substrate. Such substrates include synthetic compounds such as phenolphthalein glucuronide and methylumbelliferyl glucuronide, and metabolic products such as the glucuronides of steroids and bilirubin. However, the affinity of hydrolytic enzymes, such as $\beta$-glucuronidase, for highly polar substrates has not been described.

Wolfbeis, et al. (*Analytical Biochemistry*, Vol. 129, 365–370, 1983), describe the synthesis of esters of acetic, butyric, caprylic and oleic acids with 1-hydroxypyren-3,6,8-trisulfonic acid of the formula [I]:

wherein R is —CH$_3$, —(CH$_2$)$_2$—CH$_3$, —(CH$_2$)$_6$—CH$_3$ and —(CH$_2$)$_7$—CH=CH—(CH$_2$)$_7$—CH$_3$, respectively. Although such esters show violet fluorescence ($\lambda_{max}$ 390 and 408 nanometers) when excited below 385 nanometers, they do not fluoresce when excited at 460 nanometers. However, hydrolysis of such esters results in the formation of an anion of the formula [II]:

which exhibit both longwave excitation and emission maxima and a large Stokes' shift of 60 nanometers and have been employed as substrates for determining several hydrolases.

Fishman, et al. ("Naphthol AS-BI $\beta$-D-Glucosiduronic Acid, its Synthesis and Suitability as a Substrate for $\beta$-Glucuronidase", *J. Histochem. and Cytochem.*, Vol. 12, 298–305, 1964), describe the synthesis of naphtol AS-BI $\beta$-D-glucosiduronic acid of the formula [III]:

Fishman, et al., also describe the chemical and physical properties of the compound of the formula [III], as well as its behavior as a substrate for $\beta$-D-glucuronidase.

Bollenback, et al. (*J. Am. Chem. Soc.*, 77, 3310–3315, 1955), describe the synthesis of methyl(tri-O-acetyl-($\alpha$ and $\beta$)-D-glucopyranosyl bromide)-uronates of the formula [IV] below from glucouronolactone, as well as the synthesis of various methyl(aryl-tri-O-acetyl-($\alpha$ and $\beta$)-D-glucopyranosid)-uronates of the formula [V] below from the methyl(tri-O-acetyl-($\alpha$ and $\beta$)-D-glucopyranosyl bromide)-uronates:

Methyl (tri-O-acetyl ($\alpha$)-D-glucopyranosyl bromide)-uronate

Methyl (aryl-tri-O-acetyl ($\beta$)-D-glucopyranosyl)-uronate

The methyl(aryl-tri-O-acetyl-(H$^T$)-D-glucopyranosid)-uronates described by Bollenback, et al., include those where R in the formula [V] is phenyl, 1-naphthyl and 2-naphthyl, and the alpha anomers of the compounds of the formula [IV] and [V] where R is o-chlorophenyl, p-chlorophenyl, o-bromophenyl, p-bromophenyl, o-iodophenyl, o-tolyl, m-tolyl, p-tolyl, o-hydroxyphenyl, 1-naphthyl, 2-naphthyl, methyl gentisate and o-nitrophenyl are also described.

SUMMARY OF THE INVENTION

The present invention provides novel pyrene-trisulfonate derivatives, the synthesis of such derivatives, and the use thereof for the determination of glycohydrolytic enzyme activity. The pyrenetrisulfonate derivatives of the present invention are of the general formula [VI]:

wherein R is a carbohydrate, or a carbohydrate derivative, which is capable of binding to a glycohydrolytic enzyme and comprises from 1 to 10 linked monosaccharide units, and wherein $M_1$, $M_2$, and $M_3$, which can be the same or different, are an alkali metal, hydrogen, ammonium, alkyl-substituted ammonium, or aryl-substituted ammonium. Preferably, R is β-D-glucuronide, β-D-glucoside, β-D-galactoside, β-D-maltoside, a monosaccharide, or a disaccharide.

According to the present invention, the compound of formula [VI] does not fluoresce when excited with light having a wavelength of 460 nm, whereas the aglycon moiety thereof does fluoresce at such wavelength and, accordingly, is especially useful for the determination of glycohydrolytic enzymes. Such glycohydrolytic enzymes include, but are not intended to be limited to, β-glucuronidase, β-glucosidase, β-galactosidase, and the like. In particular, the method for determining a glycohydrolytic enzyme according to the present invention comprises the steps of:

(a) forming a test solution comprising a test sample containing the glycohydrolytic enzyme and the compound of formula VI, wherein the glycohydrolytic enzyme binds to R and causes the hydrolysis of the compound to result in the formation of free 8-hydroxy-1,3,6-pyrene trisulfonate as a function of, and which can be correlated to, the amount of the glycohydrolytic enzyme present in the test sample; and

(b) measuring and correlating either the intensity of fluorescence, or the optical density, of the test solution to the presence or amount of the glycohydrolytic enzyme in the test sample.

When performing the method according to the present invention, the test sample can be selected from a variety of fluids or tissue, which include, but are not intended to be limited to, plasma, serum, ascites fluid, lymphatic fluid, cerebral spinal fluid, nipple fluid discharge, urine, gingival crevicular fluid, and the like. The test sample can also be selected from a variety of environmental or microbiological samples such as sewage, water, soil, oil, bacterial cultures, and the like, for the detection of bacterial glycosidases (Acta Pathol. Microbiol. Scand. [B], 84B(5), pages 245-251, October 1976). It is to be understood that the test sample can be diluted in a suitable diluent buffer, such as phosphate buffered saline with serum components, to provide a sample volume that is required by a particular assay.

Where the intensity of fluorescence is measured, the test solution is excited with radiant energy having a wavelength of from between about 390 nm and about 490 nm wherein the selection of the appropriate wavelength will depend upon the pH of the test solution. Preferably, the test solution is excited with radiant energy having a wavelength of from between about 410 nm for test solutions having a pH of about 5.0 or less and about 454 nm for test solutions having a pH of about 9.0 or greater. Such radiant energy causes 8-hydroxy-1,3,6-pyrene trisulfonate to fluoresce wherein the amount of fluorescence, which is measured at a wavelength of from between about 500 nm and about 530 nm, preferably at about 515 nm, can be correlated to the amount of the glycohydrolytic enzyme present in the test sample.

Alternatively, since the presence of 8hydroxy-1,3,6-pyrene trisulfonate changes the optical density of the test solution, the optical density of the test solution can be measured and correlated to the amount of the glycohydrolytic enzyme present in the test sample. According to the present invention, such increase in optical density is measured at a wavelength of from between about 390 nm and about 490 nm wherein the selection of the appropriate wavelength will depend upon the pH of the test solution. Preferably, the optical density is measured at a wavelength of from between about 410 nm for test solutions having a pH of about 5.0 or less and about 454 nm for test solutions having a pH of about 9.0 or greater. The measured changes in the optical density are the result of the liberated form of 8-hydroxy-1,3,6-pyrene sulfonate and can be correlated to the amount of the glycohydrolytic enzyme present in the test sample.

A preferred embodiment of the present invention provides for the synthesis of pyrene-(1,3,6-trisulfonic acid)-8-β-D-glucuronide of the formula [VII]:

and the use thereof for the determination of β-D-glucuronidase. The determination of β-D-glucoronidase is particularly useful for the diagnosis of periodontal disease wherein an elevated activity thereof in gingival crevicular fluid indicates acute inflammatory response.

The compounds according to the present invention are significantly more soluble in water and aqueous systems than those substrates previously described, particularly for β-glucuronidase, and a shift in the absorption and emission spectrum between the protonated form of the dye and the glycosides enables kinetic analysis at a pH of less than about 7.0. The present invention also provides other pyrene-(1,3,6-trisulfonic acid) derivatives and the use thereof for determining other enzymes.

DETAILED DESCRIPTION OF THE INVENTION

As used herein, the pyrano ring of the compounds that are described herein is represented as a six membered heterocyclic ring composed of five carbons and one oxygen, with a line extending above and below each of the carbons. Substituents other than hydrogen are shown at the end of each line that is above or below the relevant carbon to indicate that the isomer represented has that substituent above or below, respectively, the carbon to which it is bonded. Hydrogens attached directly to the carbons of the pyrano ring are not shown but, of course, are present wherever required to satisfy the four valences of the carbons. In referring to saccharides herein, conventional numbering is used, the carbons of the pyrano ring being numbered in ascending order clockwise around the ring as viewed from above the paper on which it is represented, starting with the carbon adjacent the oxygen of the ring. For example, in the compound of formula VII, it is the 1 carbon of the pyrano ring to which the pyrene sulfonate is bonded through an ether linkage, and the bond from the 1 carbon to the oxygen of the ether linkage is above the pyrano ring. The 6 carbon is exocyclic, and is attached to the 5 carbon.

According to the present invention, the compound 1,3,6-pyrene trisulfonate-8-β-D-glucuronide [VII] is produced as described in Example 1 hereinbelow, and can be used to conduct a kinetic determination of, for example, β-glucuronidase activity. Such determination can be made by adding a 10 μL sample which contains β-glucuronidase to a 0.2 mL portion of a 0.3 mM solution of 1,3,6-pyrene trisulfonate-8-β-D-glucuronide [VII] in 0.1M sodium acetate in deionized water, mixing thoroughly, and injecting the mixed sample into a fluorimetric flow cell which is temperature controlled at about 22.5° C. while exciting at 410 nm and measuring emission at 515 nm. The initial rate of increase of fluorescence is proportional to the β-glucuronidase activity in the sample. A standard curve can be prepared from data derived by carrying out the procedure, using solutions of known, and varying, β-glucuronidase activity, and the standard curve can be used to determine β-glucuronidase activity from fluorescence data concerning unknown samples.

The 1,3,6-pyrene trisulfonate-8-β-D-glucuronide [VII] can also be used to conduct a determination of β-glucuronidase activity by a procedure which involves determining a colorimetric endpoint. This determination can be made by adding a 50 μL sample which contains β-glucuronidase to 0.2 mL of a 0.3 mM solution of 1,3,6-pyrene trisulfonate-8-β-D-glucuronide [VII] in a 0.1M solution of sodium acetate in deionized water, mixing thoroughly, incubating at 37° C. for 15 minutes, quenching the reaction by adding 1.0 mL of a 0.25M solution of glycine, pH 10.5, in deionized water, and measuring the optical density at 460 nm. The optical density is proportional to the β-glucuronidase activity of the sample. A standard curve can be prepared from data collected from solutions containing known amounts of 8-hydroxy-1,3,6-pyrene trisulfonate or from solutions containing known amounts of β-glucuronidase.

A kinetic determination of β-glucuronidase activity by absorption can also be made using 1,3,6-pyrene trisulfonate-8-β-D-glucuronide [VII]. To make this determination, a 50 μL sample which contains β-glucuronidase is added to 1.0 mL of a 0.1 mM solution of 1,3,6-pyrene trisulfonate-8-β-D-glucuronide [VII] in a 0.1M solution of sodium acetate in deionized water (pH 4.25), mixing thoroughly, and measuring optical density at 410 nm continuously in a temperature controlled cell. The initial linear rate of increase in absorbance is proportional to the enzyme activity of the sample. A standard curve can be prepared from data collected from solutions containing known amounts of 8-hydroxy-1,3,6-pyrene trisulfonate or from solutions containing known amounts of β-glucuronidase.

A fluorescence endpoint determination of β-galactosidase activity can be made using 1,3,6-pyrene trisulfonate-8-β-D-galactoside as a substrate. 1,3,6-pyrene trisulfonate-8-β-D-galactoside is prepared as set forth in Example 4 below, and is of the formula [VIII]:

1,3,6-PYRENE TRISULFONATE-8-β-GALACTOSIDE

To make this determination, 50 μL samples which contain β-galactosidase are added to 0.1 mL of a 1.0 mM 1,3,6-pyrene trisulfonate-8-β-D-galactoside [VIII] solution in 0.1M 4-morpholinepropanesulfonic acid in deionized water. After incubation for 15 minutes at ambient temperature of about 22° C., the reaction is quenched by adding 2.0 mL of 0.25M glycine, pH 10.5, vortexing each solution thoroughly, and measuring fluorescence emission at 515 nm after excitement in a fluorimetric cuvette at 454 nm. Emission at 515 nm is compared with a plot of intensity of emission at 515 nm as a function of 8-hydroxy-1,3,6-pyrene trisulfonate concentration or with a plot of intensity of emission at 515 nm as a function of β-galactosidase concentration.

A fluorescence endpoint determination of β-glucosidase activity can be made using 1,3,6-pyrene trisulfonate-8-β-D-glucoside as a substrate. 1,3,6-pyrene trisulfonate-8-β-D-glucoside is prepared as set forth in Example 3 below, and is of the formula [IX]:

To make this determination, 50 μL samples which contain β-glucosidase are added to 0.1 mL of a 1.0 mM 1,3,6-pyrene trisulfonate-8-β-D-glucoside [IX] solution in 0.1M 4-morpholinepropanesulfonic acid in deionized water. After incubation for 15 minutes at ambient temperature of about 22° C., the reaction is quenched by adding 2.0 mL of 0.25M glycine, pH 10.5, vortexing each solution thoroughly, and measuring fluorescence emission at 515 nm after excitement in a fluorimetric cuvette at 454 nm. Emission at 515 nm is compared with a plot of intensity of emission at 515 nm as a function of 8-hydroxy-1,3,6-pyrene trisulfonate concentration or with a plot of intensity of emission at 515 nm as a function of $\beta$-glucosidase concentration.

It will be appreciated that various changes and modifications can be made to the embodiments described herein without departing from the spirit and scope of the present invention. For instance, Examples 1 and 3 demonstrate the production of pyrene-(1,3,6-trisulfonic acid)-8-$\beta$-D-glucuronide [VII] and of pyrene-(1,3,6-trisulfonic acid)-8-$\beta$-D-glucoside [IX], respectively, compounds which differ from one another only with respect to the identity of the substituent on the 5 carbon, carboxyl in the former and $CH_2OH$ in the latter. The glucuronide was produced from bromo-2,3,4-tri-O-acetyl-$\alpha$-D-glucopyranuric acid methyl ester (methyl (tri-O-acetyl($\alpha$)-D-glucopyranosyl bromide)-uronate [IV]), which is commercially available, and can also be produced by a method disclosed in Bollenback et al., supra. The glucoside was produced from 2,3,4,6-tetra-O-acetyl-$\alpha$-D-glucopyranosyl bromide, which is also available commercially and, in addition, can be produced by the method of Koenigs and Knorr, *Berichte der Deutschen Chemischen Gesellschaft*, Vol. 34, pages 957–981 (1901) (see, also, *Advanced Organic Chemistry*, Fieser and Fieser, Reinhold Publishing Company, New York, 1961, pages 932 and following). It will be appreciated that the Bollenback, et al., and Koenigs and Knorr methods can be used to produce the corresponding O-acetyl bromides from other saccharides. A saccharide starting material that has a $CH_2OH$ group that is desired in the final product can be reacted with the acetyl bromide, as in Koenigs and Knorr, to produce a polyacetylated bromocarbohydrate in order to protect primary and secondary hydrolysis in the carbohydrate. A saccharide starting material that has a lactone or a carboxy group can be reacted to produce a methyl or another ester which is then reacted with the acetyl bromide, as in Bollenback, et al., to produce the corresponding O-acetyl bromide ester, which is then reacted with the pyrene sulfonate in the presence of the tetradecyl-trimethyl ammonium bromide or an equivalent. The tetradecyl-trimethyl ammonium bromide, or a suitable equivalent, is used as a phase transfer catalyst in the synthesis. In the absence of a phase-transfer catalyst, or in the presence of commonly used reagents, such as benzyltriethyl ammonium bromide (Kleine, et al., *Carbohydrate Research*, Vol. 142 (1985), 333–337), the pyrene sulfonate reacts minimally with either the acetyl bromide or the acetyl bromide ester. The O-acetyl bromide starting materials set forth in the Examples below can be produced from methyl $\alpha$-D-glucuronate (Example 1), $\alpha$-D-glucopyranose (Example 3), D-galactose (Example 4) and $\beta$-maltose (Example 5). Other saccharides that can be reacted with the acetyl bromide to produce a polyacetylated bromocarbohydrate or that can be reacted to produce a methyl or another ester which is then reacted with the acetyl bromide, as in Bollenback, et al., to produce a polyacetylated bromocarbohydrate, include the other anomers of the compounds of the present invention, other naturally occurring and synthetic sugars, e.g., erythrose, threose, ribose, arabinose, xylose, lyxose, allose, altrose, mannose, gulose, idose, talose, sucrose and lactose, the last two, like maltose, being disaccharides, and cellobiose (a disaccharide), xylan (a polysaccharide) and polyglucuronic acid (a polysaccharide), the last three occurring in nature, associated with cellulose.

It is to be understood that according to the present invention, to be suitable for use in determining glycohydrolytic enzymes, the moiety represented by R in the formula of the compounds represented herein binds to one of the enzymes. In particular, the determination of $\beta$-glucuronidase, $\beta$-galactosidase or $\beta$-glucosidase in a sample, or the 8-hydroxy-1,3,6-pyrene sulfonate equivalence of those samples, as described herein, is the result of the enzyme binding to the glucuronide, to the galactoside or to the glucoside, respectively, which causes hydrolysis thereof and the release of free 8-hydroxy-1,3,6-pyrene trisulfonate. 8-Hydroxy-1,3,6-pyrene trisulfonate fluoresces at 515 nm after being excited at 410 nm (protonated form) or at 454 nm (anionic form), and changes the optical density of the solution at 410 nm (protonated form) and at 460 nm (anionic form).

In addition to the method described herein, the compounds of the present invention are also useful in other analytical test systems which require the measurement of the amount of enzyme present therein, particularly those analytical test systems employing enzyme-labeled assay reagents. Such other analytical systems include, but are not intended to be limited to, heterogeneous and homogeneous enzyme immunoassays known in the art, such as competitive, sandwich and immunometric techniques where the amount of enzyme label in a particular fraction thereof can be measured. Generally, such immunoassay systems depend upon the ability of an immunoglobulin, i.e., a whole antibody or fragment thereof, to bind to a specific analyte wherein a conjugate comprising an antibody, or fragment thereof, to such analyte conjugated with a label or detectable moiety known in the art is employed to determine the extent of such binding. Such detectable moieties or labels include, but are not intended to be limited to, enzymes, chromogens, luminescent compounds, fluorescent compounds, and the like. Typically, the extent of binding is determined by the amount of the detectable moiety present in the conjugate which either has or has not participated in a binding reaction with the analyte, wherein the amount of the detectable moiety detected and measured can be correlated to the amount of analyte present in the test sample.

For example, where an antibody labeled with $\beta$-galactosidase is employed as a conjugate in one of such immunoassay systems, the $\beta$-galactosidase activity of the conjugate can be determined by adding a substrate solution comprising 2 mM 1,3,6-pyrene trisulfonate-8-$\beta$-D-galactosidase, 1 mM magnesium chloride, and 10 mM 2-mercaptoethanol in 0.1M potassium phosphate buffer, pH 7.0. Subsequent to the addition of the substrate, the enzyme-catalyzed hydrolysis is stopped with the addition of a volume of 2M glycine, pH 10.5. The fluorescence emission at 515 nm is measured while exciting the test solution at 454 nm wherein the amount of fluorescence of either the $\beta$-galactosidase of the conjugate which has or which has not participated in a binding reaction with the analyte can be correlated to the amount of analyte present in the test sample.

A test kit according to the present invention comprises all of the essential reagents required to perform an assay for the determination of a glycohydrolytic enzyme as described herein. The test kit is presented in a commercially packaged form as a combination of one or more containers holding the necessary reagents, as a composition or admixture where the compatibility of the reagents will allow. The test kit comprises a compound of the formula [VI], and may also include other materials as are known in the art and which may be desirable from a commercial user standpoint, such as buffers, diluents, standards, and the like. A particularly preferred test kit is for the determination of β-glucoronidase for the diagnosis of periodontal disease wherein such test kit comprises the compound of the formula [VII].

The present invention will now be illustrated, but is not intended to be limited, by the following examples. Formula numbers in brackets refer to the structural formula used throughout the specification.

EXAMPLE 1

Synthesis of Pyrene-(1,3,6-trisulfonic acid)-8-β-D-glucuronide [VII]

Pyrene-(1,3,6-trisulfonic acid)-8-β-D-Glucuronide [VII] was prepared from 8-hydroxy-1,3,6-pyrene trisulfonic acid trisodium salt (Eastman Kodak Co., Rochester, N.Y., USA) and bromo-2,3,4,-tri-O-acetyl-α-D-glucopyranuronic acid methyl ester (Sigma Chemical Co., St. Louis, Mo., USA).

5.0 g (9.5 mmol) of trisodium 8-hydroxy-1,3,6-pyrene trisulfonate is dissolved in 55 mL of aqueous 2M N-methylmorpholine. To this is added a solution of 25.5 g (75 mmol) of tetradecyl-trimethyl ammonium bromide in 50 mL of chloroform. The mixture is stirred at room temperature (22.5° C.) until homogeneous. 6.0 g (14 mmol) of bromo-2,3,4-tri-O-acetyl-α-D-glucopyranuronic acid methyl ester is then added, and the reaction mixture is stirred at 37° C. for 18 hours protected from light. Approximately 10–15 mL of an aqueous phase which formed was separted from the organic phase by centrifuging and discarded. The organic phase which remained was concentrated under vacuum until it formed a gel. The gel was then redissolved in 75 mL methanol, and a 14 g addition of solid sodium acetate was made, with stirring; stirring was continued until the sodium acetate dissolved. The solution was applied to a 5×90 cm column of LH-20 (Pharmacia LKB Biotechnology, Inc., Piscataway, N.J., USA) and eluted with methanol. The product eluted as a blue fluorescent band before the yellow-green fluorescent band of unreacted dye. The blue fluorescent fractions contained an acetyl protected intermediate product of the compound of formula [VII] wherein the $CO_2H$ group was $CO_2CH_3$, the three hydroxyls were $OOCCH_3$ groups, and the three hydrogens were sodiums) were pooled and dried by rotoevaporation.

The dried, acetyl protected intermediate product was dissolved in the sodium methoxide solution, and the solution was allowed to stand at room temperature of about 22° C. for 4 hours, after which time an addition of 2.5 mL deionized water was made, and the solution was mixed thoroughly and allowed to stand at room temperature for about 15 hours. Cold acetone was then added to the solution to precipitate crude 1,3,6-pyrene trisulfonate-8-β-D-glucuronide [VII], which was further purified by dissolving in a small amount of deionized water and precipitating with cold methanol; the final product was recovered by filtration and dried, yielding 0.4 g product, 17 percent of theory.

UV/VIS (0.25M glycine buffer, pH 10.5): max.=395 nm ($\epsilon$=21 $mM^{-1}cm^{-1}$). Acidification to pH 4.25 does not affect the spectrum.

Fluorescence: absorption max.=395 nm; emission max.=420 nm.

$^1$H-NMR ($D_2O$): $\delta$=3.7–3.85 (m, 2H); 4.0 (dd, 1H); 4.13 (d, 1H); 5.62 (d, 1H); aromatic protons: 8.55 (s, 1H); 8.94 (d, 1H); 9.08 (dd, 2H); 9.19 (d, 1H); 9.22 (s, 1H).

Mass Spectrum (High Resolution, Negative ion FAB-MS): m/e=698.9126 (M-Na)−; $C_{22}H_{14}O_{16}S_3Na_3$, calculated m/e=698.9138.

EXAMPLE 2

Assay For β-glucuronidase Employing Pyrene-(1,3,6-trisulfonic acid)-8-β-D-glucuronide [Formula VII]

Figure 1:
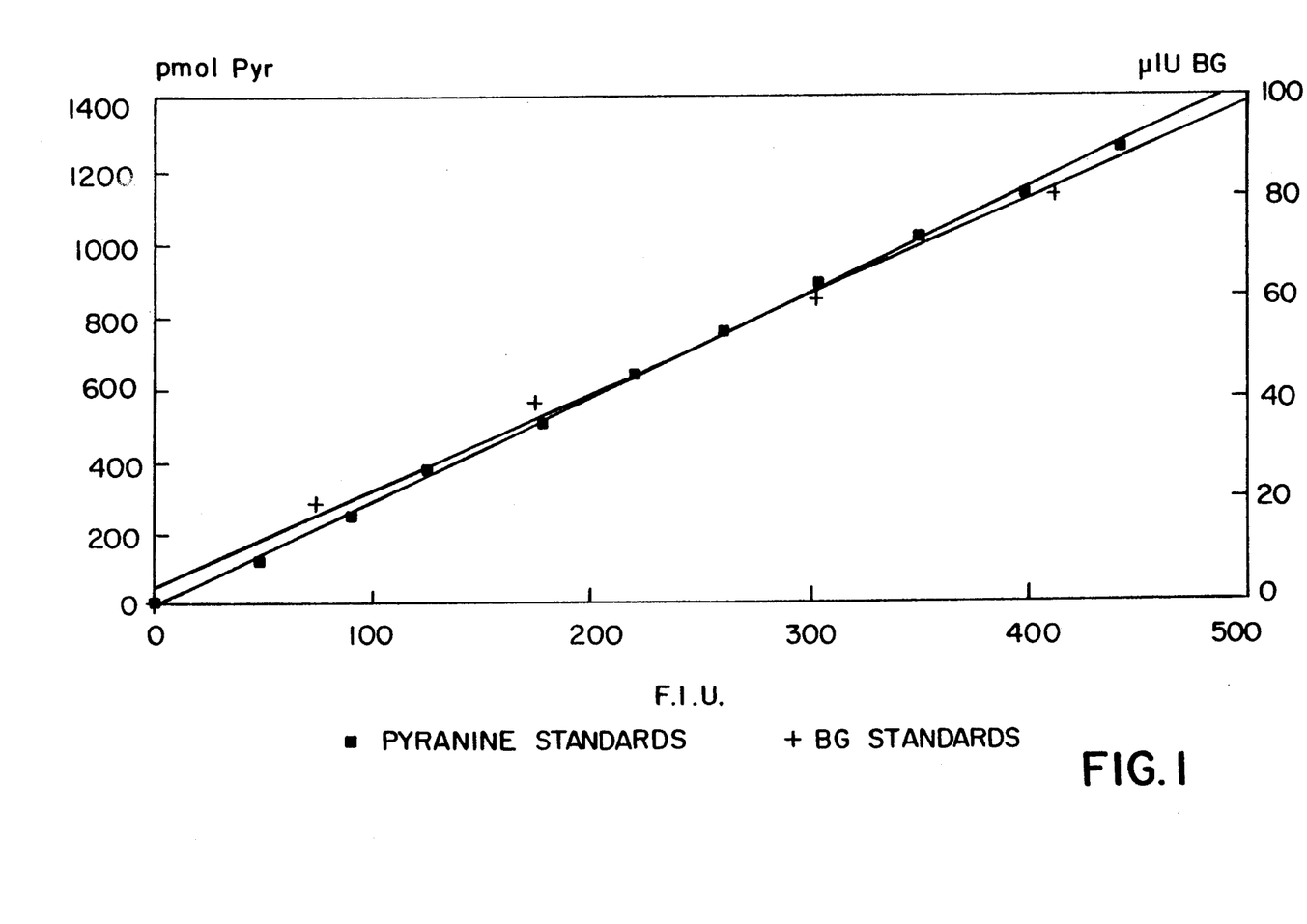
FIG. 1 illustrates an end-point fluorometric analysis for β-glucuronidase (βG) and the amount of 8-hydroxy-1,3,6-pyrene trisulfonate (Pyr) formed as an end product (βG is expressed as enzyme activity using phenophthalein β-D-glucuronic acid [uIU]).

Solutions containing known amounts of 8-hydroxy-1,3,6-pyrene trisulfonate were prepared, and 50 μL portions of each solution were mixed with 2.1 mL of 0.25M glycine (pH 10.5) and placed in fluorimetric cuvettes and excited at 454 nm. Emission at 515 nm was measured for each solution, and the data were used to prepare a plot of intensity of fluorescence emission at 515 nm as a function of 8-hydroxy-1,3,6-pyrene trisulfonate concentration. Solutions containing known amounts of β-glucuronidase were also prepared, and were used to determine fluorescence at 515 nm as a function of β-glucuronidase concentration; 50 μL portions of each solution were added to 0.1 mL of 0.3 mM 1,3,6-pyrene trisulfonate-8-β-D-glucuronide [VII] (prepared according to Example 1) in a 0.1M sodium acetate solution in deionized water, and, after incubation for 15 minutes at ambient temperature of about 22° C., the reactions were quenched by adding 2.0 mL of 0.2M glycine, pH 10.5. Each solution was then vortexed thoroughly, and fluorescence at 515 nm was measured after excitation in a fluorimetric cuvette at 454 nm. The data were used to prepare a plot of intensity of fluorescence emission at 515 nm as a function of β-glucuronidase concentration (FIG. 1). Samples containing β-glucuronidase were analyzed by adding 50 μL of each to 0.1 mL of a 0.3 mM solution of 1,3,6-pyrene trisulfonate-8-β-D-glucuronide [VII] in a 0.1M sodium acetate solution in deionized water, and, after incubation for 15 minutes at ambient temperature of about 22° C., quenching the reaction by adding 2.0 mL of 0.25M glycine, pH 10.5, vortexing each solution thoroughly, and measuring fluorescence at 515 nm after excitation in a fluorimetric cuvette at 454 nm. The 8-hydroxy-1,3,6-pyrene trisulfonate equivalence was determined by reference to the first curve (Table 1), while the β-glucuronidase content was determined by reference to the second (Table II).

TABLE I

| F.I.U. | Pyranine Standards (pmol) |
|---|---|
| 0 | 0 |
| 47 | 127 |
| 90 | 251 |
| 125 | 372 |
| 177 | 501 |
| 219 | 625 |
| 260 | 754 |
| 304 | 878 |
| 350 | 1,003 |
| 398 | 1,127 |

TABLE I-continued

| F.I.U. | Pyranine Standards (pmol) |
|---|---|
| 441 | 1,253 |

TABLE II

| F.I.U. | BG (μIU) |
|---|---|
| 0 | 0 |
| 74 | 20 |
| 174 | 40 |
| 302 | 60 |
| 412 | 80 |

EXAMPLE 3

Kinetic Determination of β-glucuronidase Activity by Fluorescence

Figure 2:
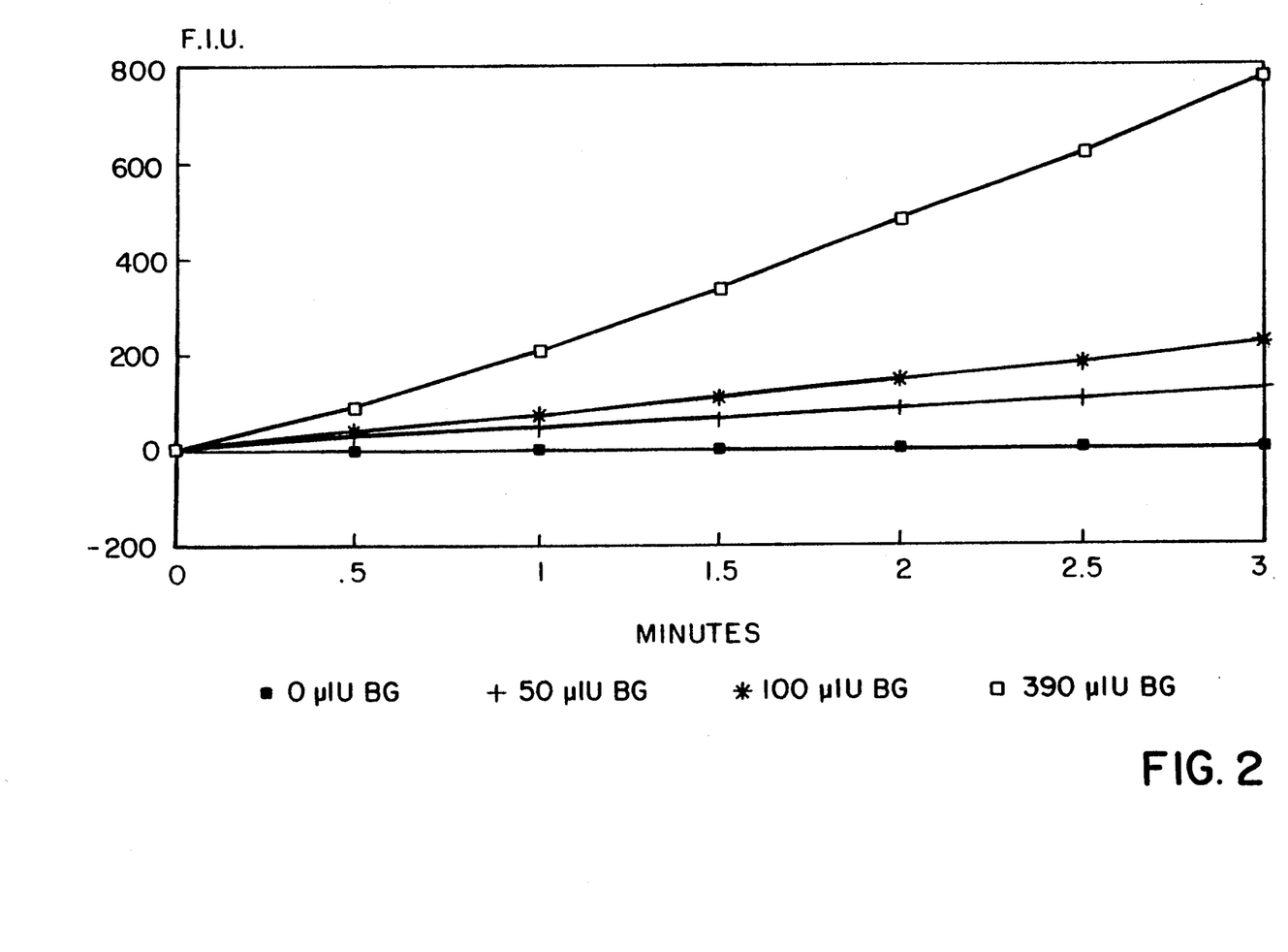
FIG. 2 illustrates a kinetic fluorometric analysis of β-glucoronidase hydrolysis of 1,3,6-pyrene trisulfonate-8-β-D-glucuronide.

A 10 μL sample, containing β-glucuronidase, is added to 0.2 mL of 0.3 mM 1,3,6-pyrene trisulfonate-8-β-D-glucuronide in 0.1M sodium acetate, pH 4.25. The solution is mixed thoroughly and then injected into a fluorimetric flow cell. The increase is fluorescence, excitation at 410 nm and emission at 515 nm, is recorded at 30 second intervals. The initial rate of fluorescence increase is proportional to the β-glucuronidase activity present in the sample. The activity may be standardized using solutions of known β-glucuronidase activity to establish an enzymatic standard curve (FIG. 2).

EXAMPLE 4

Kinetic Determination of β-glucuronidase Activity by Absorption

Figure 3:
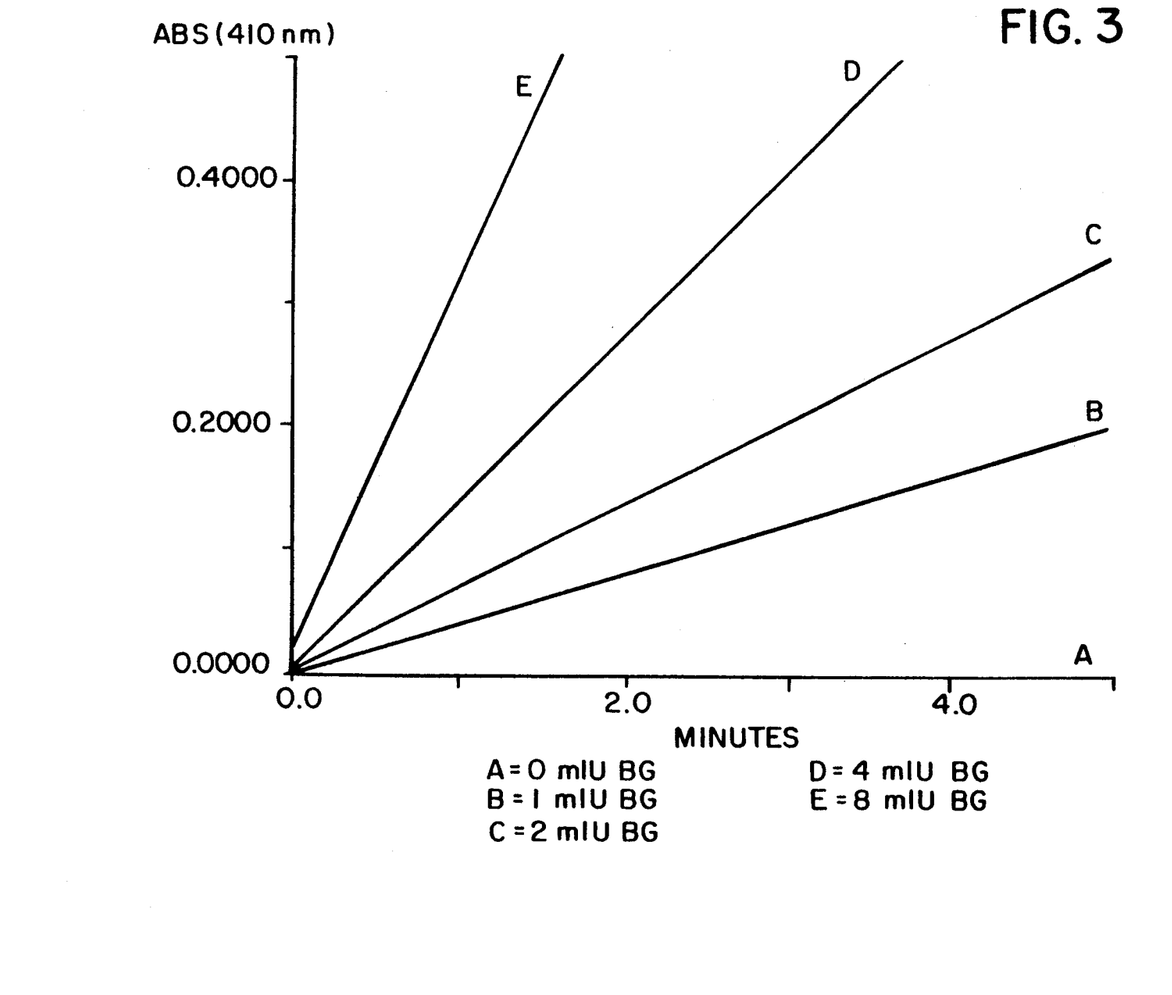
FIG. 3 illustrates a kinetic absorption analysis of β-glucuronidase hydrolysis of 1,3,6-pyrene trisulfonate-8-β-D-glucuronide.

A 50 μL sample, containing β-glucuronidase, is added to 1.0 mL of 0.1 mM 1,3,6-pyrene trisulfonate-8-β-D-glucuronidase, in 0.1M sodium acetate, pH 4.25. The solution is thoroughly mixed and the increase in optical density at 410 nm is measured continuously. The initial linear rate of increase in absorbance is proportional to the enzyme activity of the sample, which may be compared to an enzymatic standard curve prepared using solutions of known β-glucuronidase activity (FIG. 3).

EXAMPLE 5

Synthesis of 1,3,6-pyrene trisulfonate-8-β-D-glucoside [IX]

1.0 g (2 mmol) of trisodium 8-hydroxy-1,3,6-pyrene trisulfonate is dissolved in 2.4 mL of aqueous 2M sodium hydroxide. To this is added a solution of 3.2 g tetradecyl-trimethyl ammonium bromide in 6.5 mL of chloroform. The mixture is thoroughly vortexed followed by the addition of 0.6 g bromo-2,3,4,6-tetra-O-α-D-glucopyranosyl bromide (Sigma). The reaction mixture is mixed continuously at 37° C. for 15 hours, protected from light. Approximately 10–15 mL of an aqueous phase which formed was separated from the organic phase by centrifuging and discarded. The organic phase which remained was concentrated under vacuum. The residue was then redissolved in methanol (final volume=20 mL) and undissolved solids were removed by filtration. The filtrate was applied to a 2.5×55 cm column of LH-20 (Pharmacia Fine Chemicals) and eluted with methanol. The fractions contained the acetyl protected product of the compound of formula [IX] wherein the three OH groups were all O-acetyl, and the hydrogens were sodiums) were pooled and concentrated under vacuum to 5 mL. A freshly prepared 1.0M solution of sodium methoxide (1.0 mL) was added to the sample, with mixing, and the reaction mixture which resulted was allowed to stand at room temperature for 5 hours. A 5.0 mL portion of deionized water was then added, and, after stirring, the reaction mixture was allowed to stand at room temperature for about 17 hours. Solids were then removed by filtration, and the filtrate was concentrated under vacuum to 5 mL. The 1,3,6-pyrene trisulfonate-8-β-D-glucoside [IX] was then precipitated from the concentrated filtrate by an addition of cold acetone, recovered by filtration, and dried.

EXAMPLE 6

Synthesis of 1,3,6-pyrene trisulfonate-8-β-D-galactoside [XIII]

The procedure described above in Example 3 was followed to produce 1,3,6-pyrene trisulfonate-8-β-D-galactoside [XIII] by substituting 0.6 grams 2,3,4,6-tetra-O-acetyl-α-D-galactosyl bromide for bromo-2,3,4,6-tetra-O-acetyl-α-D-glucopyranosyl bromide in the procedure of Example 3.

EXAMPLE 7

Synthesis of 1,3,6-pyrene trisulfonate-8-β-D-maltoside [X]

The procedure described above in Example 3 was followed to produce 1,3,6-pyrene trisulfonate-8-β-D-maltoside [X] by substituting 1.2 g α-bromohepta-O-acetylmaltose for bromo-2,3,4,6-tetra-O-acetyl-α-D-glucopyranosyl bromide in the procedure of Example 3.

1,3,6-PYRENE TRISULFONATE-8-β-MALTOSIDE

It will be apparent that many modifications and variations of the present invention as set forth herein are possible without departing from the spirit and scope thereof, and that, accordingly, such limitations are imposed only as indicated by the appended claims.

We claim:

1. A compound of the formula:

wherein R is a carbohydrate or a carbohydrate derivative which is capable of binding to a glycohydrolytic enzyme, said carbohydrate or carbohydrate derivative comprising from 1 to 10 linked monosaccharide units, and wherein $M_1$, $M_2$, and $M_3$, which are the same or different, are an alkali metal, or hydrogen, or ammonium, or alkyl-substituted ammonium, or aryl-substituted ammonium.

2. The compound of claim 1 wherein R is β-D-glucuronide.

3. The compound of claim 1 wherein R is β-D-glucoside.

4. The compound of claim 1 wherein R is β-D-galactoside.

5. The compound of claim 1 wherein R is β-D-maltoside.

6. The compound of claim 1 wherein R is a monosaccharide.

7. The compound of claim 1 wherein R is a disaccharide.

8. A method for determining the presence of a glycohydrolytic enzyme in a test sample, said method comprising the steps of:

(a) forming a test solution comprising a test sample containing a glycohydrolytic enzyme and a compound of the formula:

wherein R is a carbohydrate or a carbohydrate derivative which is capable of binding to a glycohydrolytic enzyme, said carbohydrate or carbohydrate derivative comprising from 1 to 10 linked monosaccharide units, and wherein $M_1$, $M_2$, and $M_3$, which are the same or different, are an alkali metal, or hydrogen, or ammonium, or alkyl-substituted ammonium, or aryl-substituted ammonium; and (b) correlating the intensity of fluorescence or the optical density of the test solution to the presence of the glycohydrolytic enzyme in the test sample.

9. The method of claim 8 wherein the intensity of fluorescence of the test sample is measured and correlated to the amount of the glycohydrolytic enzyme present in the test sample.

10. The method of claim 8 wherein the optical density of the test solution is measured and correlated to the amount of the glycohydrolytic enzyme present in the test sample.

11. The method of claim 8 wherein said glycohydrolytic enzyme is selected from the group consisting of β-glucuronidase, β-glucosidase and β-galactosidase.

12. The method of claim 8 wherein said carbohydrate or said carbohydrate derivative is selected from the group consisting of D-glucuronic acid, D-glucose and D-galactose.

13. A test kit for determining the presence of a glycohydrolytic enzyme in a test sample, said test kit comprising a compound of the formula:

wherein R is a carbohydrate or a carbohydrate derivative which is capable of binding to a glycohydrolytic enzyme, said carbohydrate or carbohydrate derivative comprising from 1 to 10 linked monosaccharide units, and wherein $M_1$, $M_2$, and $M_3$, which are the same or different, are an alkali metal, or hydrogen, or ammonium, or alkyl-substituted ammonium, or aryl-substituted ammonium.

14. The test kit of claim 13 wherein said glycohydrolytic enzyme is selected from the group consisting of β-glucuronidase, β-glucosidase and β-galactosidase.

15. The test kit of claim 13 wherein said carbohydrate or said carbohydrate derivative is selected from the group consisting of D-glucuronic acid, D-glucose and D-galactose.

16. The test kit of claim 13 wherein said compound is of the formula:

Formula I and said glycohydrolytic enzyme is β-glucuronidase.

* * * * *